United States Patent
Athanikar et al.

(10) Patent No.: US 6,322,828 B1
(45) Date of Patent: Nov. 27, 2001

(54) PROCESS FOR MANUFACTURING A PHARMACEUTICAL CHEWING GUM

(75) Inventors: Narayan K. Athanikar, Irvine, CA (US); Scott A. Gubler, St. George, UT (US)

(73) Assignees: Deseret Laboratories, Inc., St. George, UT (US); Josman Laboratories, Inc., Irvine, CA (US)

( * ) Notice: Subject to any disclaimer, the term of this patent is extended or adjusted under 35 U.S.C. 154(b) by 0 days.

(21) Appl. No.: 09/394,217

(22) Filed: Sep. 13, 1999

(51) Int. Cl.$^7$ ............... A23G 3/30; A61K 9/68
(52) U.S. Cl. ............ 426/3; 424/48; 424/440; 424/441; 426/285; 426/454
(58) Field of Search ................ 426/3, 5, 285, 426/454; 424/48, 440, 441

(56) References Cited

U.S. PATENT DOCUMENTS

| | | | |
|---|---|---|---|
| 4,000,321 | 12/1976 | Mochizuki et al. | 426/5 |
| 4,161,544 | 7/1979 | Kaul | 426/5 |
| 4,370,350 | 1/1983 | Fisher et al. | 426/5 |
| 4,405,647 | * 9/1983 | Fisher et al. | 426/3 X |
| 4,753,805 | 6/1988 | Cherukuri et al. | 426/5 |
| 4,803,082 | * 2/1989 | Cherukuri et al. | 426/3 X |
| 4,971,079 | 11/1990 | Talapin et al. | 131/359 |
| 4,975,270 | * 12/1990 | Kehoe | 426/3 X |
| 5,711,961 | * 1/1998 | Reiner et al. | 426/3 X |
| 5,922,347 | 7/1999 | Hausler et al. | 424/441 |

FOREIGN PATENT DOCUMENTS

2808160 * 8/1979 (DE) ................. 426/5

* cited by examiner

*Primary Examiner*—Arthur L. Corbin
(74) *Attorney, Agent, or Firm*—Workman, Nydegger & Seeley

(57) ABSTRACT

The present invention provides a process for preparing a chewing gum tablet, in which a chewing gum composition is cooled to a temperature at which the composition is brittle, and the composition is ground while brittle to form a fine powder. In a preferred process, the composition is cooled by mixing with a coolant, such as solid carbon dioxide, and the mixture is ground to a powder. The powder can be mixed with a pharmaceutical active ingredient capable of topical absorption in the buccal cavity or in the mucous layer of the upper or lower intestinal tract, and formed into a tablet. Preferably, the mixture of the powder, pharmaceutical active ingredient, and other additives such as coating agents, binders, additional active ingredients, and sweeteners, are granulated in a fluidized bed granulator prior to forming the mixture into a tablet. The resulting tablet provides a dosage form of the pharmaceutical active ingredient having a more accurate and uniform dose of the active ingredient.

32 Claims, No Drawings

PROCESS FOR MANUFACTURING A PHARMACEUTICAL CHEWING GUM

FIELD OF THE INVENTION

The present invention relates to processes for producing chewing gum tablets as dosage forms for pharmaceutical therapeutic agents, and in particular to a process for making a pharmaceutical chewing gum dosage form having a more accurate and uniform dose of the pharmaceutical active ingredient.

BACKGROUND

Pharmaceutical therapeutic agents, such as drugs, are formulated in a variety of dosage forms, depending upon the target absorption site of the drug, the intended time profile for absorption, the solubility characteristics of the drug, the susceptibility of the drug to various forms of attack in vivo, such as enzymatic degradation and organ uptake, and other considerations well-known to those skilled in the art. A large number of drugs are formulated in orally ingestible dosage forms for delivery into the gastrointestinal tract, where they are absorbed into the blood stream and carried to various organs or tissues where the pharmacological action is exerted. Typically, such dosage forms are capsules or tablets, which may further be provided with various coatings, to assist in passage through the gastrointestinal tract, or to provide a delayed or extended release profile. When more rapid therapeutic action is desired, or when the therapeutic agent is particularly susceptible to chemical or enzymatic attack in the gastrointestinal tract, a preferred route of delivery is injection into the blood stream, and the corresponding dosage form is an injectable liquid or solution. Still other drugs are delivered topically to the skin, eyes, and various mucosal tissues, in dosage forms such as ointments, creams, gels and lotions.

A number of therapeutically useful drugs are capable of buccal absorption; i.e., absorption in the oral cavity, either sublingually or throughout the oral mucosal wall, or by dissolution in the saliva and absorption in the throat, esophagus, or upper gastrointestinal tract. For drugs having significant buccal and/or upper and lower gastrointestinal tract absorption, oral dosage forms taking advantage of the absorption, such as lozenges, chewable tablets, and chewing gum, are particularly advantageous. Such dosage forms permit more rapid therapeutic action compared to per-oral (swallowed) dosage forms, and the topically absorbed therapeutic agent also partially escapes liver metabolism.

The chewing gum dosage form is particularly attractive due to its ease of administration and the generally acceptable or even pleasant qualities of chewing gum. These attractive properties can significantly improve patient compliance with the dosage regimen. Thus, for example, U.S. Pat. No. 4,971,079 is directed to chewing gum compositions having an anti-nicotine therapeutic effect, for use in facilitating cessation of smoking. Likewise, U.S. Pat. No. 5,922,347 is directed to chewing gum compositions containing acetylsalicylic acid, a well-known anti-inflammatory and analgesic compound.

The conventional chewing gum processing technology involves melting a gum base in, for example, a sigma blender, and adding components such as sweeteners and flavorants to the melt. The melted mass is then extruded, rolled into sheets, and cut to the desired shape on the rollers. This conventional technology, however, suffers from several disadvantages, when applied to the preparation of pharmaceutical chewing gum dosage forms. For example, the elevated temperatures used in the melt can adversely affect the chemical stability of the therapeutic agent contained therein. In addition, the melting and mixing process of the highly viscous gum mass makes controlling the accuracy and uniformity of the drug dose difficult, and this difficulty is further exacerbated by the lack of a precise form, shape or weight of the dosage form. Further, the gum processing technology is not easily adapted to incorporate the stringent sanitary manufacturing conditions required for production of pharmaceutical products, and the concomitant process validation and control measures. In addition, conventional gum processing technology is generally poorly suited for high-speed, more economical, production.

Several patents are directed to improved methods of processing chewing gums, in order to overcome some of the disadvantages described above. U.S. Pat. No. 4,000,321, for example, is directed to a process for preparing chewing gum, in which a chewing gum composition is cooled to $-15°$ C. to facilitate fragmentation, and the cooled composition is pulverized with a crusher, hammer mill, pelletizer or turbomill. The pulverized product is then melted to cause the pulverized pieces to co-adhere, forming a chewing gum reportedly having low specific gravity and a soft chewing texture. The process, however, suffers from all of the disadvantages associated with heating, process speed, poorly defined dosage forms and weights described above, and is not well-suited for making a pharmaceutical chewing gum dosage form.

U.S. Pat. No. 4,753,805 is directed to a chewing gum composition in the form of a tablet having a low moisture content. The tablet is produced by grinding a chewing gum composition, blending the ground composition with a compression aid, and compressing the granulated product to form a tablet. Grinding of the chewing gum composition, typically a difficult process because of the tendency for the gum to stick to the grinding apparatus, is accomplished by the use of 2–8% by weight of a grinding aid such as an alkaline metal phosphate, an alkaline earth metal phosphate, or a maltodextrin. The use of such grinding aids, however, is disadvantageous. The metal phosphate salts are highly alkaline, and such alkalinity may be incompatible with acidic ionizable therapeutic agents, for example. In addition, the grinding aid remains in the composition and ultimately in the chewing gum tablet, and the presence of a large amount of metal phosphate in the dosage form is potentially problematic from therapeutic and safety perspectives.

Thus, there is a need for processes to produce dosage forms of buccally absorbable therapeutic agents which do not suffer from the disadvantages of conventional pharmaceutical chewing gum formulations.

SUMMARY OF THE INVENTION

It is an object of the present invention to provide a process for preparing chewing gum dosage forms of therapeutic agents topically effective toward the gastrointestinal tract having improved dose accuracy and uniformity.

It is also an object of the present invention to provide a process for preparing chewing gum dosage forms of therapeutic agents topically effective toward the gastrointestinal tract having a precise and well-defined form, shape and weight.

It is also an object of the present invention to provide a process for preparing chewing gum dosage forms of therapeutic agents topically effective toward the gastrointestinal tract, wherein the therapeutic agent is not subjected to elevated temperatures.

It is further an object of the present invention to provide processes for preparing chewing gum dosage forms of therapeutic agents topically effective toward the gastrointestinal tract capable of being carried out in high-speed, efficient manufacturing processes.

It is still a further object of the present invention to provide chewing gum dosage forms of therapeutic agents topically effective toward the gastrointestinal tract.

The foregoing objects and other advantages are achieved by the process of the present invention, in which a chewing gum composition is cooled to a temperature at which the composition is brittle, and the composition is ground while brittle to form a fine powder. In a preferred process, the composition is cooled by mixing with a coolant, such as solid carbon dioxide, and the mixture is ground to a powder. The powder can be mixed with a pharmaceutical active ingredient capable of buccal and/or upper or lower gastrointestinal tract topical absorption (i.e., topically effective toward the gastrointestinal tract), and formed into a tablet. Preferably, the mixture of the powder, pharmaceutical active ingredient, and other additives such as coating agents, binders, additional active ingredients, and sweeteners, are granulated in a fluidized bed granulator prior to forming the mixture into a tablet. The resulting tablet provides an improved dosage form of the pharmaceutical active ingredient.

Thus, in one aspect, the present invention provides a process for preparing a chewing gum tablet, the process including the steps of cooling a chewing gum composition to a temperature at which the composition is brittle, grinding the cooled chewing gum composition, and forming the ground chewing gum composition into a tablet.

In another aspect, the present invention provides a process for preparing a chewing gum tablet, the process including the steps of providing a mixture including a chewing gum composition and solid carbon dioxide, grinding the mixture to form a powder, removing the solid carbon dioxide from the powder, and forming the powder into a tablet.

In another aspect, the present invention provides a process for preparing a dosage form of an active ingredient topically effective toward the gastrointestinal tract, the process including the steps of providing a mixture including a chewing gum composition and solid carbon dioxide, grinding the mixture to form a powder, removing the solid carbon dioxide from the powder, mixing the powder with a composition including the active ingredient to form an active ingredient-containing powder, granulating the active ingredient-containing powder in a fluidized bed granulator, and compressing the granules into a tablet to form a dosage form containing the active ingredient.

In another aspect, the present invention provides a chewing gum dosage form of an active ingredient topically effective toward the gastrointestinal tract, the dosage form including a gum base and an active ingredient and being formed of a plurality of compressed granules containing the gum base and active ingredient.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The present invention is directed to processes for improved production of pharmaceutical chewing gum dosage forms. The processes of the present invention enable production of chewing gum tablets without the disadvantages of heating the therapeutic agent, and without problems associated with inaccuracy and non-uniformity of therapeutic agent doses characteristic of conventional chewing gum processes. The present invention achieves these and other significant advantages by a process in which a chewing gum composition is cooled to a brittle temperature, ground while at a brittle temperature to form a powder, and formed into a tablet. The pharmaceutical therapeutic agent, or active ingredient, is readily mixed with the powdered gum composition prior to tablet formation, to produce a uniform and accurate mixture, from which a well-defined and precise tablet dosage form can be prepared by tabletization.

In one step of the process of the present invention, a chewing gum composition is cooled to a temperature at which the composition is brittle. The chewing gum composition can be any chewing gum composition, such as conventional compositions known in the art. In general, such compositions include a chewing gum base, to which may be added flavorants, sweeteners, colorants, and other ingredients known in the art. The chewing gum base is typically a natural or synthetic elastomer, such as rubber, chicle, lechi caspi, jelutong, polyisobutylene, an isobutylene-isoprene copolymer, a styrene-butadiene copolymer, or other suitable gum base known in the art. In order to facilitate the subsequent grinding step, the chewing gum composition is preferably in the form of chips, pellets, or other relatively small particles.

The chewing gum composition is cooled to a temperature at which the composition is brittle. It should be appreciated that even a mildly cooled chewing gum composition will possess some degree of brittleness; however, to be suitable for the process of the present invention, the composition is cooled to a temperature at which the composition is sufficiently brittle such that the brittleness is maintained during the subsequent grinding step without adhesion to the grinding apparatus. The appropriate temperature is determined in part by the specific composition of the chewing gum, and is easily determined empirically by observing the properties of the cooled chewing gum composition. Thus, for example, a chewing gum composition cooled to a temperature sufficiently low can be ground in, for example, a mill grinder, without the composition sticking to the grinder parts. Preferably, the temperature will be less than −15° C., more preferably less than −30° C., and still more preferably less than about −40° C.

The cooling can be carried out by any of a variety of cooling processes. The chewing gum composition can be frozen in a conventional freezer apparatus capable of reaching the very low temperatures needed to achieve the requisite brittleness. Preferably, however, the chewing gum composition is cooled by contacting with a coolant. The coolant can be any substance capable of cooling the chewing gum composition to the desired temperature and can be, for example, a cryogenic liquid such as liquid nitrogen, a cold solid such as solid carbon dioxide, or a cold gas such as the gaseous boil-off from a cryogenic liquid. The coolant should be chosen so that the coolant does not interact adversely with the chewing gum composition or with the mixing or grinding apparatuses used in the present process. In addition, the coolant should not produce a substance upon warming that suffers from such adverse interactions, or that leaves a residue that adversely affects subsequent processing or presents potential safety hazards when the chewing gum tablet is chewed. For example, a coolant such as water ice, even if cooled to a sufficiently low temperature, would not be preferred, as any water ice that melts will form liquid water, which is absorbed by the chewing gum composition. Likewise, a coolant such as a hydrocarbon slush would not be preferred, since any hydrocarbon residue remaining in the chewing gum composition would present potential safety hazards when the chewing gum tablet is consumed.

In accordance with the present invention, and in a particularly preferred aspect, it has been surprisingly found that by mixing a chewing gum composition with solid carbon dioxide (dry ice), the chewing gum composition can be cooled to a brittle temperature without the undesirable effects discussed above. At the sublimation temperature, −78.5° C., solid carbon dioxide is sufficiently cold to ensure that the chewing gum composition is suitably brittle. Of course, the solid carbon dioxide can be cooled to an even lower temperature, if desired. Upon warming, the solid carbon dioxide sublimes to form carbon dioxide gas, which does not react with the chewing gum composition, is not absorbed by the composition, and does not interact adversely with processing apparatuses. Further, the gaseous, non-reactive nature of the sublimation product ensures that no undesirable and potentially hazardous residue of the coolant remains in the chewing gum tablet product. Preferably, the solid carbon dioxide coolant is provided in pelletized form to facilitate further processing steps.

Alternatively, the steps of cooling the chewing gum composition and grinding the composition can be combined into a single step by, for example, cooling the grinding apparatus itself, such as by contacting the grinding apparatus with a coolant. For example, in this alternative aspect, the grinding apparatus can be placed in a cooling jacket of liquid nitrogen or other cold liquid. For more efficient cooling, in this embodiment, the chewing gum composition is preferably pre-cooled, although the pre-cooling need not be to a temperature as low as the brittle temperature. It should be appreciated that even in the preferred embodiment, wherein the chewing gum composition is cooled my mixing with a coolant, it may also be advantageous to cool the grinding apparatus as well.

If desired, the chewing gum composition can be mixed with an anti-caking agent prior to the grinding step, and the use of an anti-caking agent is preferred. Such anti-caking agents are known in the art. A preferred anti-caking agent is precipitated silicon dioxide. In a preferred embodiment in which the chewing gum composition is mixed with solid carbon dioxide and an anti-caking agent prior to grinding, the anti-caking agent helps to prevent agglomeration of the subsequently ground chewing gum particles, upon sublimation of the solid carbon dioxide.

If a coolant, such as solid carbon dioxide, and other components, such as an anti-caking agent are used, the chewing gum composition and other substances can be combined using a conventional mixing apparatus, such as a vented V-blender.

The chewing gum composition, and other components such as coolant and anti-caking agent, are ground to form a fine powder. The grinding can be carried out using any conventional grinding apparatus, such as a mill grinder. In a preferred embodiment, a mixture of a chewing gum composition, solid carbon dioxide, and precipitated silica is provided, and the mixture is introduced into a mill grinder. In this embodiment, the mixture is ground to a fine powder, and the solid carbon dioxide remains present during the grinding process. It has been surprisingly found that by co-grinding the chewing gum composition and solid carbon dioxide, the chewing gum composition can be ground into a fine powder, without any adverse adhesion to the grinding apparatus.

The desired properties of the ground chewing gum composition are better achieved when the composition is kept at a very low temperature throughout the grinding process. Thus, in a particularly preferred process, a mixture of chewing gum composition, solid carbon dioxide and precipitated silica is ground in a mill grinder in a first grinding step, additional solid carbon dioxide and precipitated silica are added to the ground composition, and the composition is further ground in a second grinding step. This two-step grinding process advantageously keeps the chewing gum composition at a very low temperature. Although not wishing to be bound by theory, it is further believed that the presence of the solid carbon dioxide particles, in addition to providing the necessary cooling, also serves to enhance the efficiency of the grinding process. It should be appreciated that although a two-step grinding process is described herein, the number of steps is not particularly limited. Thus, a process in which additional solid carbon dioxide and/or precipitated silica are added in multiple steps, or even in a slow, continuous stream, may also be used if desired.

After the composition is ground to a powder, the coolant can be removed by, for example, allowing the coolant to evaporate. Using the preferred coolant of solid carbon dioxide, the coolant is removed simply by allowing the solid carbon dioxide to sublime, releasing harmless carbon dioxide gas and leaving no undesirable contaminants. The ground composition can be stored such that the carbon dioxide gas can escape, as for example in loosely closed plastic bags. Alternatively, the carbon dioxide can be removed more rapidly by processing the ground composition in a fluidized bed reactor.

Once the coolant has been removed from the powder, the powder can be mixed with other ingredients as desired, before forming the powder into a tablet. Such ingredients can be any ingredient known to be incorporated into chewing gum and not incompatible with tablet formation, such as coating agents, binders, lubricants, sweeteners and the like. Preferably, a pharmaceutical active ingredient topically effective toward the gastrointestinal tract is added in an amount such that the tablet ultimately formed includes a therapeutically effective dose of the active ingredient. As used herein, the term "topically effective toward the gastrointestinal tract" means having significant absorption in the buccal cavity and/or the mucous layer of the upper and/or lower gastrointestinal tract. The active ingredient can be any active ingredient having such topical absorption, such as, for example, gastrointestinal anti-infective drugs, anti-diarrheal drugs, anti-cholic drugs, cardiovascular drugs such as nitroglycerin, and calcium channel blocking agents such as nifedipine.

Such ingredients can be combined with the powder by blending, in for example, a sigma mill, or a high shear mixer. If a conventional blending apparatus is used, the powder mixture should include sufficient amounts of binder to enable effective processing of the mixture. Such binders, well-known in the art, are typically aqueous, and the large amounts of aqueous binder necessary to enable tabletization from a blended mixture are not preferred, as the mixture tends to swell and to develop a disadvantageous stickiness that makes tabletization less efficient. However, although not preferred, such blending processes can still be used in the process of the present invention.

In a preferred process, it has been surprisingly found that the powdered chewing gum composition produced by the process described above can be combined with other ingredients, such as coating agents, binders, sweeteners and active ingredients, in a fluidized bed reactor. The use of a fluidized bed reactor is particularly advantageous, as the process partially rebuilds the powder into granules, as well as coats the powder particles and/or granules with a coating agent, thereby minimizing undesired particle agglomeration. In this embodiment, the temperature of the process should be controlled. If the temperature is too low, the mixture (the "blend") will stick because of a low evaporation rate as the binding solution is sprayed on the blend. The granules that develop are then too large for subsequent tabletization. If the temperature is too high, the blend can soften, with the same disadvantageous results. With these considerations in mind, one skilled in the art can readily determine the appropriate process temperature by observing and optimizing the properties of the granules produced. To reduce the processing time, the fluid bed granulator can be pre-heated to the chosen processing temperature prior to adding the powder mixture. After granulation, the granulate can be discharged onto screens, and any granules that are too large can be removed.

In a preferred process, the powder mixture, containing the powdered chewing gum composition, active ingredient, and other additives, is weighed into individual "charges" for the fluid bed granulator. After processing as described above, and screening, the individual charges are then preferably recombined and mixed in a V-blender, and the resultant "cross-blend" is then discharged across a screen to again remove any granules that are too large. It is particularly advantageous to sample the cross-blend discharge by taking multiple samples from the discharge stream, for analysis of the active ingredient. Thus, the discharge mixture can be stored while the multiple samples are analyzed, to insure that the desired level and uniformity of level of active ingredient are present. If necessary, additional active ingredient can then be added.

The discharge mixture is again placed in a V-blender, and any additional active ingredient added. In addition, an anti-adherent is preferably added at this time, along with any other desired excipients or inactive ingredients. A preferred anti-adherent is talc. The mixture can then be discharged, again screened, and staged for compression.

Compression to form tablets can be carried out by any conventional process, such as a punching process. Of course, the punching process should be monitored for signs of sticking to the punches, and the apparatus cleaned, and/or coated with additional anti-adherent as needed.

In another aspect, the present invention is directed to chewing gum dosage forms of a pharmaceutical active ingredient topically effective toward the gastrointestinal tract, the dosage form being a tablet formed of compressed granules of a gum base and the active ingredient. The granules forming the tablet can be of a size convenient for tabletization, typically from about 15 to about 30 mesh size, and preferably about 20 to about 25 mesh size. The tablets can be produced by any of the methods described above. Advantageously, the tablet does not contain any residue of a grinding aid, such as an alkaline phosphate.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A process for preparing a chewing gum tablet, the process comprising:

(a) cooling a chewing gum composition to a temperature at which the composition is brittle;

(b) grinding the cooled chewing gum composition to form a chewing gum powder;

(c) mixing the chewing gum powder with a composition comprising a pharmaceutical therapeutic active ingredient to form an active-containing powder;

(d) granulating the active-containing powder to form active-containing granules; and (e) forming the active-containing granules into a tablet.

2. The process of claim 1, wherein the step of cooling the chewing gum composition comprises contacting the composition with a coolant, wherein the coolant is a non-reactive substance capable of cooling the chewing gum composition to the brittle temperature.

3. The process of claim 2, wherein the coolant is solid carbon dioxide.

4. The process of claim 1, wherein the step of grinding the cooled chewing gum composition is carried out in the presence of a coolant in contact with the chewing gum composition, wherein the coolant is a non-reactive substance.

5. The process of claim 4, wherein the coolant is solid carbon dioxide.

6. The process of claim 1, wherein the steps of cooling and grinding are carried out by mixing the chewing gum composition with solid carbon dioxide and grinding the chewing gum and solid carbon dioxide mixture.

7. The process of claim 6, wherein the chewing gum composition is mixed with solid carbon dioxide and an anti-caking agent.

8. The process of claim 1, wherein the cooling and grinding steps are carried out by:

(i) providing a mixture of the chewing gum composition, solid carbon dioxide, and an anti-caking agent;

(ii) grinding the mixture in a first grinding step;

(iii) adding additional amounts of solid carbon dioxide and anti-caking agent to the ground mixture; and (iv) further grinding the mixture in a second grinding step.

9. The process of claim 8, wherein the anti-caking agent is precipitated silicon dioxide.

10. The process of claim 1, wherein the chewing gum composition is cooled to a temperature below $-30°$ C.

11. The process of claim 1, wherein the chewing gum composition is cooled to a temperature below about $-40°$ C.

12. The process of claim 1, wherein the step of granulating is carried out in a fluid bed granulator.

13. The process of claim 12, further comprising coating the active-containing powder in the fluid bed granulator with a coating agent.

14. The process of claim 1, wherein the active ingredient is topically effective toward the gastrointestinal tract.

15. The process of claim 1, wherein the active-containing granules have an average size of about 15 mesh to about 30 mesh.

16. A process for preparing a chewing gum tablet, the process comprising:

(a) providing a mixture comprising a chewing gum composition and solid carbon dioxide;

(b) grinding the mixture to form a chewing gum powder;

(c) removing the solid carbon dioxide from the chewing gum powder;

(d) mixing the chewing gum powder with a composition comprising a pharmaceutical therapeutic active ingredient to form an active-containing powder;

(e) granulating the active-containing powder in a fluidized bed granulator to form active-containing granules; and (f) forming the active-containing granules into a tablet.

17. The process of claim 16, wherein the mixture in step (a) further comprises an anti-caking agent.

18. The process of claim 17, wherein the ant-caking agent is precipitated silicon dioxide.

19. The process of claim 17, wherein the grinding step comprises:

(i) grinding the mixture in a first grinding step;

(ii) adding additional amounts of solid carbon dioxide and anti-caking agent to the ground mixture; and (iii) further grinding the ground mixture in a second grinding step to form the chewing gum powder.

20. The process of claim 16, wherein the step of removing the solid carbon dioxide from the chewing gum powder comprises storing the chewing gum powder for a sufficient time such that substantially all of the solid carbon dioxide sublimes.

21. The process of claim 16, wherein the step of removing the solid carbon dioxide from the chewing gum powder comprises processing the chewing gum powder and the solid carbon dioxide in a fluid bed granulator.

22. The process of claim 16, wherein the chewing gum powder is mixed with a coating agent prior to the step of granulating.

23. The process of claim 16, wherein the active ingredient is topically effective toward the gastrointestinal tract.

24. The process of claim 16, wherein the active-containing granules have an average size of about 15 mesh to about 30 mesh.

25. A process for preparing a dosage form of a pharmaceutical therapeutic active ingredient, the process comprising:

(a) providing a mixture comprising a chewing gum composition, an anti-caking agent, and solid carbon dioxide;

(b) grinding the mixture to form a chewing gum powder;

(c) removing the solid carbon dioxide from the chewing gum powder;

(d) mixing the chewing gum powder with a composition comprising the pharmaceutical therapeutic active ingredient to form an active-containing powder;

(e) granulating the active-containing powder in a fluidized bed granulator to form active-containing granules; and (f) compressing the active-containing granules into a tablet to produce a dosage form containing the active ingredient.

26. The process of claim 25, wherein the anti-caking agent is precipitated silicon dioxide.

27. The process of claim 25, wherein the grinding step comprises:

(i) grinding the mixture in a first grinding step;

(ii) adding additional amounts of solid carbon dioxide and anti-caking agent to the ground mixture; and (iii) further grinding the ground mixture in a second grinding step to form the chewing gum powder.

28. The process of claim 25, wherein the step of removing the solid carbon dioxide from the chewing gum powder comprises storing the chewing gum powder for a sufficient time such that substantially all of the solid carbon dioxide sublimes.

29. The process of claim 25, wherein the step of removing the solid carbon dioxide from the chewing gum powder comprises processing the chewing gum powder and the solid carbon dioxide in a fluid bed granulator.

30. The process of claim 25, wherein the composition in step (d) further comprises a coating agent.

31. The process of claim 25, wherein the composition in step (d) further comprises at least one additive selected from the group consisting of binders, coating agents, sweeteners, and additional active ingredients.

32. The process of claim 25, wherein the active-containing granules have an average size of about 15 mesh to about 30 mesh.

* * * * *